US012491099B2

(12) United States Patent
Cohen et al.

(10) Patent No.: US 12,491,099 B2
(45) Date of Patent: Dec. 9, 2025

(54) INTRAGASTRIC EXPANDABLE DEVICES

(71) Applicant: Epitomee Medical Ltd., Caesarea (IL)

(72) Inventors: Gil Cohen, Jerusalem (IL); Valery Artamonov, Ashdod (IL); Dan Hashimshony, Pardes Hana (IL)

(73) Assignee: Epitomee Medical Ltd., Caesarea (IL)

( * ) Notice: Subject to any disclaimer, the term of this patent is extended or adjusted under 35 U.S.C. 154(b) by 221 days.

(21) Appl. No.: 18/255,838

(22) PCT Filed: Dec. 2, 2021

(86) PCT No.: PCT/IL2021/051438
§ 371 (c)(1),
(2) Date: Jun. 2, 2023

(87) PCT Pub. No.: WO2022/123555
PCT Pub. Date: Jun. 16, 2022

(65) Prior Publication Data

US 2024/0041627 A1 Feb. 8, 2024

Related U.S. Application Data

(60) Provisional application No. 63/122,235, filed on Dec. 7, 2020.

(51) Int. Cl.
*A61F 5/00* (2006.01)

(52) U.S. Cl.
CPC ............ *A61F 5/003* (2013.01); *A61F 5/0036* (2013.01)

(58) Field of Classification Search
CPC ............................... A61F 5/003; A61F 5/0036
See application file for complete search history.

(56) References Cited

U.S. PATENT DOCUMENTS

| | | | | |
|---|---|---|---|---|
| 5,750,585 | A | 5/1998 | Park et al. | |
| 2009/0182424 | A1 | 7/2009 | Marco et al. | |
| 2020/0054568 | A1* | 2/2020 | Gross | A61K 9/4808 |

FOREIGN PATENT DOCUMENTS

| | | | |
|---|---|---|---|
| CN | 1802181 | A | 7/2006 |
| JP | 2014-042833 | A | 3/2014 |
| WO | WO 98/51408 | A1 | 11/1998 |
| WO | WO 2006/092789 | | 9/2006 |
| WO | WO 2007/136735 | A2 | 11/2007 |
| WO | WO 2013/183058 | A2 | 12/2013 |

(Continued)

OTHER PUBLICATIONS

International Search Report and Written Opinion for corresponding PCT Appl No. PCT/IL2021/051438, dated Mar. 10, 2022.

*Primary Examiner* — Richard G Louis
(74) *Attorney, Agent, or Firm* — Fish & Richardson P.C.

(57) ABSTRACT

The disclosure provides a biodegradable device, administered to a patient in a compact ingestible encapsulated form. The device is self-expandable in the stomach upon contact with liquid, to assume an expanded, voluminous configuration within the stomach. The devices have a folded configuration in which intake is facilitated by the patient, and are designed to unfold and self-expand in the stomach after intake due to expansion of a plurality of expandable zones that comprise one or more gel-forming materials. The disclosure provides such devices, methods of their manufacture, as well as base units thereof.

19 Claims, 12 Drawing Sheets

(56) References Cited

FOREIGN PATENT DOCUMENTS

| | | | |
|---|---|---|---|
| WO | WO 2015/083171 | A1 | 6/2015 |
| WO | WO 2016/172054 | A1 | 10/2016 |
| WO | WO 2020/035857 | A1 | 2/2020 |

* cited by examiner

INTRAGASTRIC EXPANDABLE DEVICES

CROSS-REFERENCE TO RELATED APPLICATIONS

This application is a national stage of and claims priority under 35 U.S.C. § 371 to PCT Application No. PCT/IL2021/051438, filed on Dec. 2, 2021, which claims priority to U.S. Provisional Application No. 63/122,235, filed on Dec. 7, 2020. The contents of both of these priority applications are hereby incorporated by reference in their entirety.

TECHNOLOGICAL FIELD

This disclosure concerns ingestible intragastric devices, specifically expandable, self-deployed devices.

BACKGROUND ART

References considered to be relevant as background to the presently disclosed subject matter are listed below:

WO 2006/092789
WO 2007/136735
WO 2013/183058
WO 2015/083171

Acknowledgement of the above references herein is not to be inferred as meaning that these are in any way relevant to the patentability of the presently disclosed subject matter.

BACKGROUND

Obesity and overweight have become one of the major risk factors for morbidity and mortality. Due to medical and psychosocial impacts of being overweight, as well as the difficulty in changing eating habits, patients often find it hard to maintain diet and physical activity regimens.

One of the approaches to induce weight loss is by reducing the stomach volume and/or increasing the feeling of satiety, either by invasive procedures (such as bariatric surgery) or by administration of devices that deploy in the stomach. Ingestible devices that deploy in the stomach provide temporary reduction of stomach volume, as well as increased satiation by applying pressure onto the stomach walls, thus inducing a feeling of a fuller stomach although smaller quantities of food are being consumed. These devices are designed to reside in the stomach for a pre-determined time period, followed by degradation to allow the device to pass through the pylorus (a barrier between the gastric and intestine) to the intestine for natural expulsion from the body.

GENERAL DESCRIPTION

This disclosure provides a biodegradable device, administered to a patient in a compact ingestible encapsulated form. The device is self-expandable in the stomach upon contact with liquid (e.g. water, gastric fluid), to assume an expanded, voluminous configuration within the stomach. The device in its expanded form is designed to reside in the stomach for a pre-defined period of time before undergoing degradation. The devices are designed for fast and effective expansion, controlled by the folding arrangement of the device in its compact, folded form. Thus, the devices of this disclosure assume a compact folded configuration that can easily be swallowed by a patient, and significantly change shape and increase in volume within the stomach to induce an increase in satiety.

Thus, in one of its aspects, this disclosure provides a biodegradable self-expandable device having a first folded state and an expanded state. The device comprises a thin annular base unit that is divided into a plurality of consecutive (i.e. continuous) segments along the circumference of the annular base unit. The annular base unit comprises a plurality of first and second fold axes, such that each segment is defined between a pair of successive first fold axes, and each segment comprising one second fold axis. The first and second fold axes are alternatingly arranged along the circumference of the unit.

One or more of the plurality of segments include one or more zones that comprise at least one gel-forming material, the gel-forming material in each zone is substantially encapsulated between at least two layers of liquid-permeable material.

In the first folded state of the device, the segments are folded such that the first fold axes extend along a common axis, and each folded segment assumes a loop-like conformation with the second fold axis defining an apex of the loop-like conformation, and with the folded segments being substantially stacked one over the other (i.e. the loops are arranged one on top of the other, with regards to the thin film thickness dimension, and substantially parallel one another). In the expanded state of the device, the first fold axes are distanced one from the other.

The gel-forming material is configured for swelling upon contact with liquid (e.g. liquid in the stomach that permeates through the liquid-permeable layers after ingestion of the device) to irreversibly switch the device from the first folded state to the expanded state.

In other words, in the first folded state, the device is folded such that the loops formed by the folded segments are stacked one over the other, with the first fold axes being substantially coaxial, and the apexes of the loop-like folded segments being defined by the second fold axes (each second fold axis defines an apex of a loop-like folded segment) extend opposite the first fold axes, resulting in a fan-like or flower-like configuration, with the loops being stacked one over the other.

When the device is ingested, liquid permeates through the layers of liquid-permeable material to contact the gel-forming material encapsulated in the zones of the device, thereby causing swelling (i.e. expansion) of the gel-forming material. Thus, contact of liquid with the zones causes increase in volume of the gel-forming material, pushing the loop-like folded segments against and away from one another to cause unfolding the loop-like folded segments—thus obtaining the expanded state of the device. At its expanded state, the device generally assumes it basic annular shape, thus reducing the volume of the stomach and/or applying pressure onto the walls of the stomach to increase a feeling of fullness.

By varying the type, number, geometry, distribution, etc. of the zones, as well as the dimensions of the segments, different expansion rates and expanded shapes can be obtained. Further, by folding the device along alternating first and second axes and obtaining loop-like folded segments, control over the exposure of the gel-forming material in the zones to the liquid in the stomach can be obtained, thus controlling the overall expansion rate of the device within the stomach.

It is emphasized, that the first folding axes do not overlap the second fold axes. In other words, the first and second fold axes are alternately arranged along the circumference (or perimeter) of the annular base unit and are distanced from one another along the circumference.

The term thin as used throughout the present disclosure is meant to denote an element having a thickness dimension (T) that is significantly smaller than the length (L) and width (W) of the element (T≤L, T<W). For example, a thin annular base unit means to denote a base unit having a thickness significantly smaller than the other dimensions of the unit.

In some embodiments, the width-to-thickness ratio of the annular base unit is at least larger than 6 (W/T>6), at times large than 10 (W/T>10), or even larger than 20 (W/T>20). In other embodiments, the length-to-thickness ratio of the annular base unit is at least larger than 6 (L/T>6), at times large than 10 (L/T>10), or even larger than 20 (L/T>20). In some other embodiments, both the width-to-thickness ratio and the length-to-thickness ratio of the annular base unit are at least larger than 6 (W/T>6 and L/T>6).

The term strip referred to an elongated thin piece of material (i.e. a piece with its length being larger than its width, and its width being larger than its thickness (L>W>T)), defined between two end portions, and extending along a longitudinal axis. The strip can have a substantially uniform width along its entire length or can have a varying width.

In some embodiment, when referring to a thin strip, the width-to-thickness ratio of the thin strip is at least 10 (W/T>10), at times at least 20 (W/T>20), and the length-to-width ratio of the strip is at least 3 (L/W>3), at times at least 6 (L/W>6), or even at least 10 (L/W).

By some embodiments, the device may further have a second folded state, in which the device is rolled in a direction from the common axis towards the apexes. The device in its secondary state can be encapsulated within a gastric degradable shell.

According to another aspect of this disclosure, there is provided an encapsulated biodegradable self-expandable device having a primary folded state, a secondary folded state and an expanded state, and a gastric degradable shell encapsulating the device in its secondary folded state. The device comprises a thin annular base unit that is divided into a plurality of consecutive segments along the circumference of the unit; alternating first and second fold axes, each segment being defined between a pair of consecutive first fold axes and each segment comprises one second fold axis; and one or more segments in the plurality of segments comprise one or more zones that comprise at least one gel-forming material, the gel-forming material in each zone is encapsulated between at least two layers of liquid-permeable material. In the primary folded state of the device, the segments are folded such that the first fold axes extend along a common axis, and each folded segment assumes a loop-like conformation with the second fold axis defining an apex of the loop-like conformation, with the folded segments being substantially stacked one over the other. In the secondary folded state of the device, the device is further rolled in a direction from the common axis towards the apexes. In the expanded state, the first fold axes are distanced one from the other. The gel-forming material is configured for swelling upon contact with liquid, such that swelling of the gel-forming material upon contact with liquid in the stomach after ingestion irreversibly switches the device from the secondary folded state to the expanded state (at least partially through the primary folded state).

When the encapsulated device is ingested, the gastric degradable shell is first degraded in order to expose the device. Once contacted with liquid in the stomach, the swelling of the gel-forming material in the zones causes the device to at least partially unroll from its secondary folded state. Then, as described above, the device can assume its expanded state upon further swelling of the gel-forming material in the zones.

In the expanded state, the device may have a circular shape, a polygonal shape, or an irregular shape. Typically, in its expanded state in the stomach, the device can assume a three-dimensional (3D) shape generally conforming to the shape of at least a section of the stomach.

In some embodiments, the annular base unit is formed out of a thin strip that has a longitudinal axis, with the first and the second fold axes alternatingly arranged along and perpendicular to the longitudinal axis.

Typically, the strip has a substantially uniform thickness along its length, apart from the zones (which are typically thicker).

In some embodiments, the strip extends between matching end portions, the end portions being configured for attachment one to the other to form the annular base unit. The matching end portions may, be some embodiments, be configured to form an attachment region when attached one to the other, the attachment region having a thickness substantially the same as the thickness of the strip.

In other embodiments, the annular thin base unit is planar, i.e. being a substantially 2D annular-shaped object, having a width bounded by two concentric boundaries.

The term annular is meant to denote a base unit having a continuous closed shape/contour surrounding a void. The annular base unit need not necessarily be circular; by some embodiments, the annular base unit a circular (i.e. ring like), polygonal (e.g. triangular, rectangular, trapezoidal, deltoidal, pentagonal, hexagonal, heptagonal, etc.), or of irregular shape. The annular base unit may be symmetrically or asymmetrically shaped.

As noted, the zones are formed out of substantially a monolayer of the gel-forming material sandwiched between at least two layers of liquid-permeable material. According to some embodiments, the other areas of the annular base unit (i.e. areas of the annular base unit which are not zones), may be formed out of a liquid-permeable material. Within the context of the present disclosure, the term liquid-permeable material is meant to denote a material (compound or composition of matter) that permits diffusion or passage of liquid therethrough. In order to permit degradation of the device after a predefined period of time, the liquid-permeable material is typically biodegradable, preferably enterically degradable. For example, the liquid permeable material may be perforated or porous.

According to some embodiments, the liquid-permeable material may comprise one or more compounds selected from hypromellose phthalate, cellulose acetate phthalate, hypromellose acetate succinate, cellulose acetate, ethylcellulose, polymethylmethacrylate, polymethylacrylate, polyethylacrylate, polyvinyl acrylate phthalate, polyvinyl acetate, shellac, carboxymethylcellulose, carboxyethylcellulose carboxymethylethylcellulose (CMEC), and any combinations thereof.

The liquid-permeable material may, according to some embodiments, further comprise at least one binder, plasticizer, pore-former, emulsifier, film-former, and any combinations thereof.

The term biodegradable is meant to denote any type of decomposition of the device that is caused by exposure to biological conditions after ingestion. The term encompasses mechanical breakdown, chemical or physical degradation, chemical or physical decomposition, or any other type of destruction of the integrity of the device during its passage through the gastrointestinal tract for expulsion from the body.

The annular base unit has space-apart regions, referred to herein as zones, which, as noted above, comprise the gel-forming material and distributed along segments of the unit.

In some embodiments, the gel-forming material in the zones is in the form of a gel film (i.e. a substantially continuous layer of gel). According to some embodiments, the gel-forming material is in the form of gel particles. By other embodiments, the gel forming particles are in the form of a gel film, the gel particles embedded within a matrix forming a film. In some embodiments, the gel forming particle in the gel film are arranged in substantially a monolayer of gel particles.

According to other embodiments, the gel forming-material is a composition comprising a matrix embedding a monolayer of swellable particles. According to yet other embodiments, the gel-forming material can be in the form of a powder. The average diameter of the particles of the gel-forming material can range between about 100 μm and about 300 μm (micrometers).

According to some embodiments, each of the zones comprises a different gel-forming material. In other embodiments, at least some zones comprise different gel-forming materials than others of the zones. In some other embodiments, all of the zones comprise the same gel-forming material.

The term gel-forming material is meant to denote a compound or a composition that is capable of absorbing liquid(s), thereby forming a three-dimensional voluminous network of molecules. The gel-forming material may form a physical gel (i.e. a gel in which molecules are held in the network by physical forces) or a chemical gel (i.e. a gel in which molecules are chemically bonded one to the other to form the network structure). By some embodiments, the gel-forming material comprises one or more gel forming compounds. By other embodiments, the gel-forming material comprises one or more additives.

According to some embodiments, the gel-forming material comprises one or more polymers. According to other embodiments, the gel-forming material may be charged or neutral.

According to some other embodiments, the gel-forming material is cross-linked or is cross-linkable. Without wishing to be bound by theory, the molecular weight of the gel-forming material and the degree of cross-linking have significant impact on the gel's consistency (e.g. hardness or rigidity), as well as on its rheological properties (e.g. viscosity). Hence, various molecular weights and cross-linking degrees are some of the parameters that can be used to control the behavior of the zones, thereby controlling the rate of deployment and/or the expanded size of the device within the stomach.

In some embodiments, the gel-forming material may be selected from gelatin, alginate, chitosan, dextran, collagen, hyaluronic-acid, polyglutamic-acid, elastin, calcium polycarbophil, acrylamides, styrene maleic anhydride, polyethylene oxide, polyacrylic-acid, polyethylene glycol, carboxy methyl cellulose, polyvinyl pyrrolidone, sodium polyacrylate, hydroxypropyl methylcellulose or any combination or composition thereof.

By some embodiments, the gel-forming material is a composition comprising at least one charged gel-forming compound and at least one compound having an opposite charge, constructing a PEC (Poly Electrolyte Complex) upon liquid adsorption. In some embodiments, said at least one charged gel-forming compound is selected from polyvinyl acetate diethyl amino acetate (AEA), poly-lysine, chitosan, polymethacrylate (Eudragit E), poly-arginine and any mixture thereof. In other embodiments, said opposite charged compound is selected from gelatin, hyaluronic-acid, sodium polyacrylate, heparin, polyacrylic acid (Carbomer), alginate, pectin, carboxymethylcellulose and any mixture thereof.

In some other embodiments, the gel-forming material is at least one super absorbent polymer (SAP). The term "super absorbent polymer" refers to a polymer (typically cross-linked) or a polymer composition, that can absorb and retain large quantities of liquids, such as water (or liquids containing water), relative to the dry mass of the polymer. Non-limiting examples of SAPs are polyethylene glycol (PEG), polyglutamic acid (PGA), polyacrylamide, alginic-acid, dextran, polyacrylic acid, carboxymethylcellulose (CMC), pullulan, starch, and any combinations thereof.

In some other embodiments, the gel-forming material has a swelling ratio of about 10 to 100 times-fold (w/w) (under conditions of gastric pH, at 37° C. for 1 hour).

The term swelling ratio denotes the expansion extent of the gel-forming material between the state prior to adsorbing liquid (i.e. dry or semi dry form) and after adsorbing the maximal possible amount of liquid. The swelling ratio is by weight-based and calculated according to the following equation:

$$[(\text{wet weight})-(\text{dry weight})]/[(\text{dry weight})]$$

As noted, the annular base unit is divided into a plurality of consecutive (continuous) segments. The segments can have the same length or different lengths. At least some of the segments comprise one or more of said zones; when a segment comprises more than one zone, the zones are being arranged in a spaced-apart manner (i.e. distanced one from the other) within the segment. The zones can be evenly distributed (i.e. equally spaced) with each of the segment; alternatively, the distances between zones can vary between the segments or even between zones within a single segment.

As noted, defined in the strip are first and second fold axes, which are alternatingly arranged along the circumference of the annular base unit. The term fold axis (or any lingual variation thereof) denotes a line, typically perpendicular to the longitudinal axis of the strip or directed towards a center-point of the planar annular base unit, about which portions of the unit can be folded as will now be explained. The fold axes can be physical lines indicated or formed on the annular base unit, or can be virtual (i.e. not marked and/or physically formed on the unit).

First fold axes are defined between the segments; in other words, two consecutive segments define between them a first fold axis (an alternative definition is that each segment is defined between a pair of consecutive first fold axes). For each of the segments, a second fold axis is defined as a fold axis within the span of the segment, i.e. between a pair of consecutive first fold axes.

In the primary folded state, each of the segments forms a loop-like conformation, with the first axes that define the segments being stacked one over the other, typically forming a common axis of the primary folded state. The second fold axis, that is formed within the segment, forms an apex of the loop-like conformation.

The term loop-like conformation denotes a substantially closed shape, which has a substantially closed contour. Depending on the location of the second fold axis, the loop-like conformation can be mirror-symmetrical about a plane extending between the common axis and second fold axis, or can be non-symmetrical.

Further, in the primary folded state, the folded segments are arranged such that all of the first fold axes extend along a common axis of the folded device (in fact, the first folded axes can be regarded as substantially coextending about a common axis). The folded segments are, thus, stacked one over the other. In some embodiments, the folded segments, in the primary folded state, are arranged parallel along a plane defined between the common axis and the second fold axes.

Once folded segments are stacked one over the other, the device can be easily further folded into one or more secondary folded states in order to further compact the device. According to some embodiments, the device in its primary folded state can be further rolled in a direction from the common axis towards the apexes of the loop-like folded segments, thus obtaining a secondary folded state. This secondary folded state permits further reduction of the device's size when folded to afford for encapsulation of the folded device within a gastric degradable shell, e.g. a capsule.

The gastric degradable shell typically has a size that is suitable for swallowing, e.g. of about "elongated 000" or 000 or 00 capsule or less (i.e. outer diameter of about 9.97 mm or less, height or locked length of about 30.0 mm or less and actual volume of about 1.68 ml or less). Table 1 below provides non-limiting capsule sizes suitable for use as gastric degradable shells.

TABLE 1

Degradable shell (capsule) sizes

| Capsule size | Outer Diameter (mm) | Height or Locked Length (mm) | Actual Volume (ml) |
|---|---|---|---|
| Elongated 000 | 9.97 | 30.0 | 1.68 |
| 000 | 9.97 | 26.14 | 1.37 |
| 00 | 8.53 | 23.30 | 0.95 |
| 0 | 7.65 | 21.70 | 0.68 |
| 1 | 6.91 | 19.40 | 0.50 |
| 2 | 6.35 | 18.00 | 0.37 |
| 3 | 5.82 | 15.90 | 0.30 |
| 4 | 5.31 | 14.30 | 0.21 |
| 5 | 4.91 | 11.10 | 0.13 |

As noted, a device according to some embodiments, is constructed from an annular base unit that is formed out of a thin strip. This strip (also referred to herein as a preliminary unit) is also an aspect of this disclosure. Thus, in another aspect, there is provided a preliminary unit in the form of a thin strip having a longitudinal axis, the base unit being constructed of porous material that encapsulates regions of at least one gel-forming material, the regions being spaced-apart along the longitudinal axis, each region defining a zone with the gel-forming material in each zone being encapsulated between at least two layers of liquid-permeable material, the gel-forming material being configured for swelling upon contact with liquid, and the preliminary unit being configured for forming an annular base unit that is foldable into a biodegradable self-expandable device.

In some embodiments, the strip extends between matching end portions, the end portions being configured for attachment one to the other to form said annular base unit. The matching end portions may, by some embodiments, be configured to form an attachment region when the end portions are attached one to the other, the attachment region having a thickness substantially the same as the thickness of the strip.

In some embodiments, the matching end portions are connected one to the other by overlapping the matching end portions one over the other, followed by joining the overlapped regions to each other. In other embodiments, the matching end portions are connected one to the other by overlapping the matching end portions side-by-side.

In some other embodiments, each of the end portions comprises at least two layers of liquid-permeable material, one of which extending shorter than the other along the end portion, such that the longer layer forms a single-layer terminal section of the end portion. In such embodiments, the end portions are connectable one to the other by overlapping the single-layer terminal sections side-by-side or one over the other to obtain a joint section having an overall thickness of two layers.

In some embodiments, the preliminary unit (or the strip) may be divided into a plurality of consecutive segments along the longitudinal axis, with alternating first and second fold axes, each of the first fold axes defined between adjacent segments and each segment comprises one second fold axis, and one or more segments in the plurality of segments comprise one or more zones.

By another aspect there is provided a biodegradable self-expandable device having a primary folded state and an expanded state, the device comprising a thin annular base unit formed out of a strip having a longitudinal axis, with first and second fold axes alternatingly arranged along and perpendicular to the longitudinal axis, the strip being divided into a plurality of consecutive segments, such that each pair of consecutive first fold axes define therebetween a segment and each segment comprises one second fold axis, and one or more segments in the plurality of segments include one or more zones that comprise at least one gel-forming material with the gel-forming material in each zone being encapsulated between at least two layers of liquid-permeable material; in the primary folded state of the device, the segments are folded such that the first fold axes extend along a common axis, and each folded segment assumes a loop-like conformation with the second fold axis defining an apex of the loop-like conformation, with the folded segments being substantially stacked one over the other, and the gel-forming material being configured for swelling upon contact with liquid, to irreversibly switch the device from the primary folded state to the expanded state in which the first fold axes are distanced one from the other.

By another aspect, there is provided a biodegradable self-expandable device having a primary folded state and an expanded state, the device comprising a thin planar annular base unit, divided into a plurality of consecutive segments along a circumference of the unit, each segment being defined between a pair of successive first fold axes, and each segment comprising one second fold axis, the first and second fold axes being alternatingly arranged along the circumference of the unit, and one or more segments in the plurality of segments include one or more zones that comprise at least one gel-forming material with the gel-forming material in each zone being encapsulated between at least two layers of liquid-permeable material; in the primary folded state of the device, the segments are folded such that the first fold axes extend along a common axis, each folded segment assumes a loop-like conformation with the second fold axis defining an apex of the loop-like conformation, with the folded segments being substantially stacked one over the other, and the gel-forming material being configured for swelling upon contact with liquid, to irreversibly switch the device from the primary folded state to the expanded state in which the first fold axes are distanced one from the other.

By another one of its aspects, this disclosure provides a method for producing a biodegradable self-expandable device as described herein. The method comprises:

(a) joining two opposite matching ends of a thin strip to form a thin annular base unit, the strip having a longitudinal axis and is divided into a plurality of consecutive segments along the longitudinal axis, with one or more segments in the plurality of segments comprising one or more zones, each zone comprising at least one gel-forming material configured for swelling upon contact with liquid, the gel-forming material in each zone being encapsulated between at least two layers of liquid-permeable material; and (b) folding the annular base unit along first and second fold axes alternatingly arranged along the longitudinal axis of the strip, each of the first fold axes defined between adjacent segments and each segment comprises one second fold axis, thereby obtaining a primary folded state in which the segments are folded such that the first fold axes extend along a common axis, and each folded segment assumes a loop-like conformation with the second fold axis defining an apex of the loop-like conformation, with the folded segments being substantially stacked one over the other.

By another aspect, this disclosure provides an alternative method of producing a biodegradable self-expandable device as described herein. The method comprises:

(a') folding a thin strip that has a longitudinal axis and divided into a plurality of consecutive segments along the longitudinal axis defined between two opposite matching ends of the strip, said folding being along first and second fold axes alternatingly arranged along the longitudinal axis of the strip, each of the first fold axes being defined between adjacent segments and each second fold axis being defined in a segment, one or more segments in the plurality of segments comprising one or more zones, each zone comprising at least one gel-forming material configured for swelling upon contact with liquid, and the gel-forming material in each zone being encapsulated between at least two layers of liquid-permeable material; and (b') joining the two opposite matching ends of the strip, thereby obtaining a primary folded state of a thin annular base unit formed from the strip, in which the segments are folded such that the first fold axes extend along a common axis, and each folded segment assumes a loop-like conformation with the second fold axis defining an apex of the loop-like conformation, with the folded segments being substantially stacked one over the other.

Joining the two matching ends of the strip in order to obtain the annular base unit can be carried out by any suitable joining method, e.g. mechanical interlocking, adhering, heat welding, solvent welding, suturing, etc.

By yet another aspect, there is provided a method of producing a biodegradable self-expandable device, the method comprising folding a thin planar annular base unit along first and second fold axes alternatingly arranged along the circumference of the unit, the unit being divided into a plurality of consecutive segments along said circumference such that each segment is defined between a pair of successive first fold axes, and each segment comprises one second fold axis, thereby obtaining a primary folded state in which the segments are folded such that the first fold axes extend along a common axis, and each folded segment assumes a loop-like conformation with the second fold axis defining an apex of the loop-like conformation, with the folded segments being substantially stacked one over the other, one or more segments in the plurality of segments comprising one or more zones, each zone comprising at least one gel-forming material configured for swelling upon contact with liquid, the gel-forming material in each zone being encapsulated between at least two layers of liquid-permeable material.

According to some embodiments, the methods of this disclosure can further comprise rolling the device in its primary folded state in a direction from the common axis towards the apexes, thereby obtaining a second folded state of the device.

According to a further embodiment, the methods of this disclosure comprise encapsulating the device in its second folded state within a gastric degradable shell.

By a further aspect, there is provided a method of producing an encapsulated biodegradable self-expandable device as described herein. The method comprises:

(i) joining two opposite matching ends of a thin strip to form a thin annular base unit, the strip having a longitudinal axis and is divided into a plurality of consecutive segments along the longitudinal axis, with one or more segments in the plurality of segments comprising one or more zones, each zone comprising at least one gel-forming material configured for swelling upon contact with liquid, the gel-forming material in each zone being encapsulated between at least two layers of liquid-permeable material;

(ii) folding the annular base unit along first and second fold axes alternatingly arranged along the longitudinal axis of the strip, each of the first fold axes defined between adjacent segments and each segment comprises one second fold axis, thereby obtaining a primary folded state in which the segments are folded such that the first fold axes extend along a common axis, and each folded segment assumes a loop-like conformation with the second fold axis defining an apex of the loop-like conformation, with the folded segments being substantially stacked one over the other;

(iii) rolling the device in its primary folded state about the common axis to obtain a second folded state of the device; and (iv) encapsulating the device in its second folded state within a gastric degradable shell to obtain said encapsulated biodegradable self-expandable device.

By yet a further aspect, there is provided a method of producing an encapsulated biodegradable self-expandable device as described herein. The method comprises:

(i') folding a thin strip that has a longitudinal axis and divided into a plurality of consecutive segments along the longitudinal axis defined between two opposite matching ends of the strip, said folding being along first and second fold axes alternatingly arranged along the longitudinal axis of the strip, each of the first fold axes being defined between adjacent segments and each second fold axis being defined in a segment, one or more segments in the plurality of segments comprising one or more zones, each zone comprising at least one gel-forming material configured for swelling upon contact with liquid, the gel-forming material in each zone being encapsulated between at least two layers of liquid-permeable material;

(ii') joining the two opposite matching ends of the strip, thereby obtaining a primary folded state of a thin annular base unit formed from the strip, in which the segments are folded such that the first fold axes extend along a common axis, and each folded segment assumes a loop-like conformation with the second fold axis defining an apex of the loop-like conformation, with the folded segments being substantially stacked one over the other;

(iii') rolling the device in its primary folded state about the common axis to obtain a second folded state of the device; and (iv') encapsulating the device in its second folded state within a gastric degradable shell to obtain said encapsulated biodegradable self-expandable device.

By yet a further aspect, there is provided a method of producing an encapsulated biodegradable self-expandable device as described herein. The method comprises:

(i") folding a thin planar annular base unit along first and second fold axes alternatingly arranged along the circumference of the unit, the unit being divided into a plurality of consecutive segments along said circumference such that each segment is defined between a pair of successive first fold axes, and each segment comprises one second fold axis, thereby obtaining a primary folded state in which the segments are folded such that the first fold axes extend along a common axis, and each folded segment assumes a loop-like conformation with the second fold axis defining an apex of the loop-like conformation, with the folded segments being substantially stacked one over the other, one or more segments in the plurality of segments comprising one or more zones, each zone comprising at least one gel-forming material configured for swelling upon contact with liquid, the gel-forming material in each zone being encapsulated between at least two layers of liquid-permeable material;

(ii") rolling the device in its primary folded state about the common axis to obtain a second folded state of the device; and (iii") encapsulating the device in its second folded state within a gastric degradable shell to obtain said encapsulated biodegradable self-expandable device.

By another aspect, this disclosure provides a method of reducing volume of a stomach of a subject, the method comprising administering to the subject an encapsulated self-expandable biodegradable device as described herein.

By yet another aspect of this disclosure, there is provided a method of increasing satiety of a subject, the method comprising administering to the subject an encapsulated self-expandable biodegradable device as described herein.

By yet a further aspect of this disclosure, there is provided a method of promoting weight loss of a subject, the method comprising administering to the subject an encapsulated self-expandable biodegradable device as described herein.

Without wishing to be bound by theory, it is stipulated that a device of the invention is able to stimulate the mechanoreceptors on the stomach's wall thereby simulating a feeling of stomach fullness (as felt after eating a typical meal) in the treated patient and thus suppressing patient appetite for a predetermined, limited, period of time. It is further stipulated that the simulation of a feeling of stomach fullness is achieved by use of devices of this disclosure so that it induces stomach detention and slows stomach emptying period (thereby also prolonging the intervals between meals-time periods).

In all methods described herein, said device may be administered concomitantly, sequentially, or simultaneously with any other treatment method for either curbing appetite, promoting satiety, and/or weight loss in a patient (including but not limited to administration of additional active agent, participation in an exercise and/or diet program of said patient and participation in a psychological treatment of said patient).

In another one of its aspects, this disclosure provides a kit comprising an encapsulated biodegradable self-expandable device as defined herein and instructions for use.

In a further aspect there is provided a kit comprising an encapsulated biodegradable self-expandable device as defined herein, and an ingestible degradation formulation for accelerating degradation of the device in the stomach. The ingestible degradation formulation may be a slow-release or delayed release formulation administered concomitantly with the device, such that degradation in the stomach is commenced after a predefined period of time. Alternatively, the degradation formulation may be administered after a predefined period of time from ingestion of the device.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

In the following, exemplary devices according to this disclosure will be described. While the specific examples show the device as being substantially symmetric and having a certain number of rectangular zones, it is to be understood that any number and shape of zones can be used, at any distribution along the segments. The device need not assume a symmetrical primary folded shape, as described hereinabove. Further, the elements of the device are shown out of scale for ease of illustration.

Figure 1A:
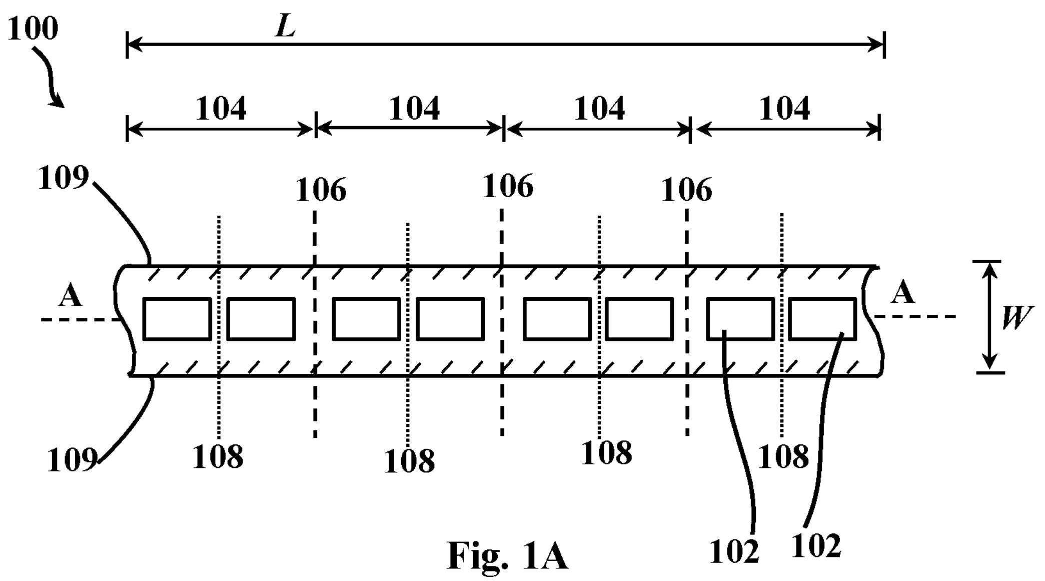
FIGS. 1A-1C are schematic representations of a top view (FIG. 1A) and side views (FIGS. 1B, 1C) of sections of annular base units constituting the device according to embodiments of this disclosure.
Figure 1B:
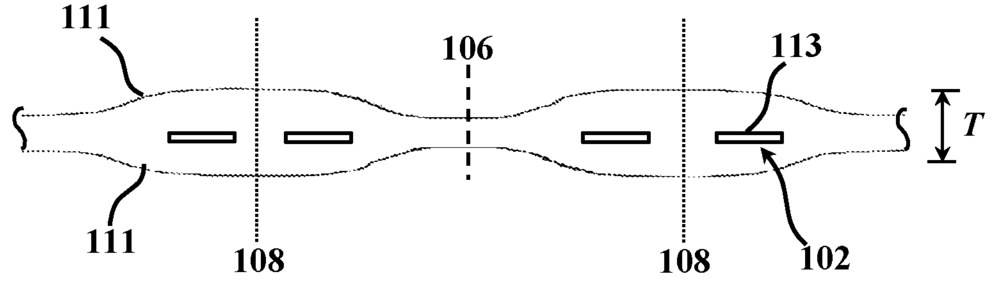
Figure 1C:
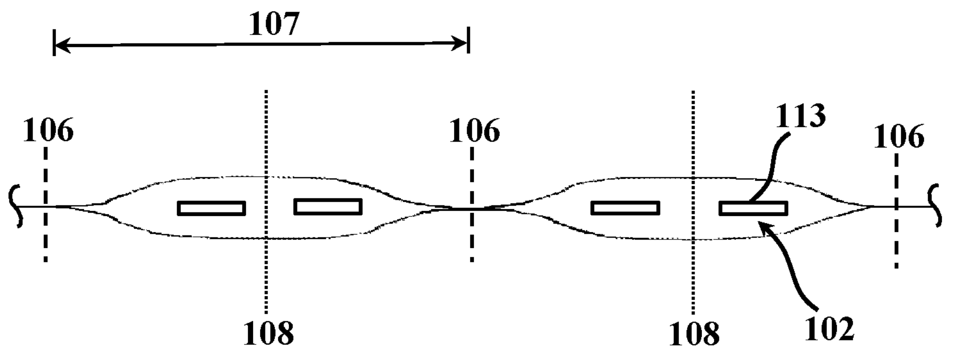

Turning first to FIGS. 1A-1C, shown are schematic representations of a section of the annular base unit of the device. FIG. 1A provides a top view of the section, FIGS. 1B-1C provide side views though section A-A of FIG. 1A. Section 100 is made of a liquid-permeable degradable material, with a plurality of zones 102 are distributed along the length of section 100. The annular base unit is typically made of two or more layers of liquid permeable material, attached, seamed, or welded to one another at edges 109 (shown in FIG. 1A, and for convenience purposes not shown in the rest of the figures). Zones 102 are typically formed out of the liquid-permeable material layers 111 that sandwich between them, at discrete regions, a film of gel-forming material 113. Alternatively, the section can be made of a monolithic liquid-permeable material, forming pockets in which the gel-forming material is encapsulated at discreate regions that form the zones.

The annular base unit is in the form of a thin strip. That is, the length (L) of the thin strip is significantly larger than its width (W), (e.g. L/W>3, 6, 10), and the thickness (7) of the thin strip is significantly smaller than its width, (e.g. W/T>10, 20).

The section 100 is divided into a plurality of consecutive segments 104, with a first fold axis 106 defined between each two adjacent segments. Each segment also comprises a second fold axis 108. As each segment 104 comprises only one second fold axis 108, the first and second axes are alternatingly arranged along the length of the section.

As seen in FIGS. 1B and 1C, the section 100 of the annular base unit does not need to have a uniform thickness. For example, as shown in FIG. 1B, section 100 can have a given thickness at the location of first fold axis 106, while having a larger thickness in zones 102. In the example of FIG. 1C, at the position of the first fold axis 106, the liquid-permeable material layers are attached one to the other, forming compartments 107 that comprise one or more zones.

Figure 1D:
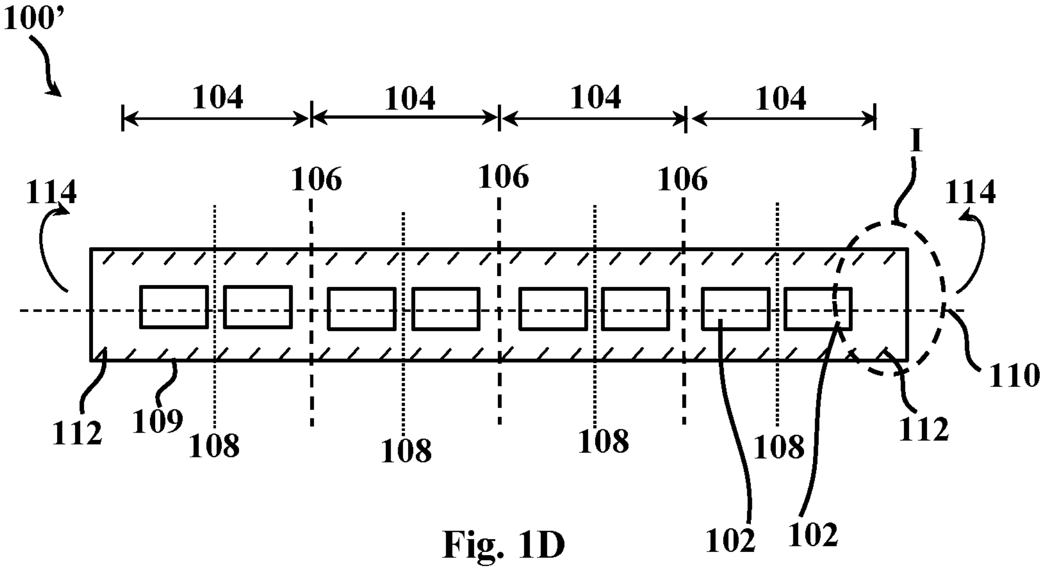
FIGS. 1D-1E are schematic representations of a top view (FIG. 1D) and a side view (FIG. 1E) of a preliminary unit (strip) for forming an annular base unit of the device and of configurations for joining "ends" of strips according to an embodiment of this disclosure.
Figure 1E:

Shown in FIGS. 1D-1E, shown is a schematic representation of a primary unit in the form of a strip 100' (that is constituted by section 100), from which the annular base unit according to an embodiment of this disclosure of the device can be constructed. Strip 100' has a thin elongated shape, extending along longitudinal axis 110 between two, opposite matching end portions 112. The zones 102 are distributed along the length of the strip 100'. Ends portions 112 can be designed in different configurations, as shown in the examples represented in FIGS. 1F(i)-1I(iv).

Figure 1F:
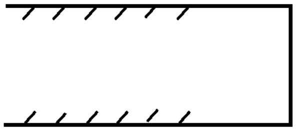
FIGS. 1F-1H show various configurations of detail I in FIG. 1D, demonstrating different configurations of the strip end portions when the strip comprises two liquid-permeable material layers.
Figure 1G:
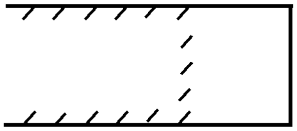
Figure 1H:
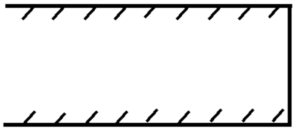
Figure 1I:
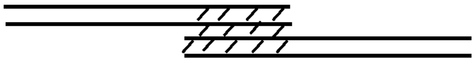
FIGS. 1I-1L show various configurations of connecting the strip end portions of FIGS. 1F-1H.
Figure 1J:
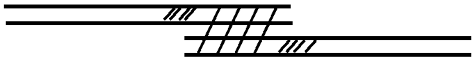
Figure 1K:
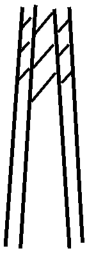
Figure 1L:
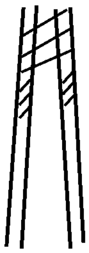

FIGS. 1F-1H show configurations of detail I in FIG. 1D, demonstrating different configurations of the strip ends, when the strip comprises two liquid-permeable material layers. As can be seen, the two layers are typically welded to one another at different locations in order to form the strip. The welding can be along the entire length of the strip, leaving the terminal edge unwelded (FIG. 1H), or welding can be carried out to leave terminal sections of the strip unconnected to one another (FIGS. 1F-1G). The end portions 112 of the strip can be connected to one another by various configurations. By overlap (such as those shown in FIGS. 1I and 1J), or side-by-side (as seen, for example, in FIGS. 1K and 1L).

Figure 1M:
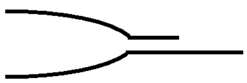
FIGS. 1M-1N show various configurations of detail II in FIG. 1E, demonstrating different configurations of the strip end portions, when the strip comprises a single liquid-permeable material layer as a terminal section of the strip end portions.
Figure 1N:
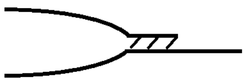
Figure 1O:
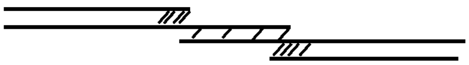
FIGS. 1O-1R show various configurations of connecting the strip end portions of FIGS. 1M-1N.
Figure 1P:
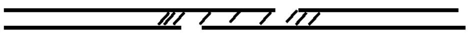
Figure 1Q:
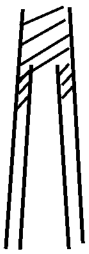
Figure 1R:
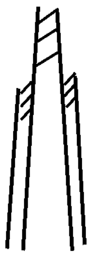

FIGS. 1M-1N show configurations of detail II in FIG. 1E, demonstrating additional configurations of the strip end portions, when the strip comprises two liquid-permeable material layers of different lengths at the end portion 112 of the strip, resulting in a single-layer terminal section of the end portion 112 (as shown in FIGS. 1M and 1N). As shown, the two layers can be welded along their overlapping area, leaving a terminal single layer exposed permitting its joining to the opposite strip end portion 112, as can be seen in FIG. 1N. For joining opposing ends of the strip, the two single-layer terminal sections of the end portions can be brought into overlap with one another (as shown in FIGS. 1O-1P) or side-by-side (seen in FIGS. 1Q-1R), welding together the single-layer terminal sections of the end portions.

Figure 1S:
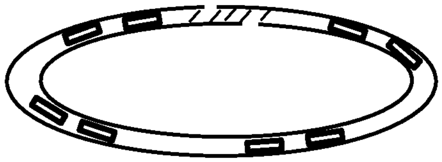
FIG. 1S is an exemplary annular base unit, in which the strip ends are joined by the configuration of FIG. 1P.

Once folded in the direction of arrows 114 the matching end portions 112 are brought together and further joined/attached/connected to each other, for example as shown on FIG. 1S. The primary unit now forms the annular base unit of a device according to an embodiment this disclosure, with the segments, zones, first fold axes and second fold axes arranged along the circumference of the annular base unit.

Figure 2A:
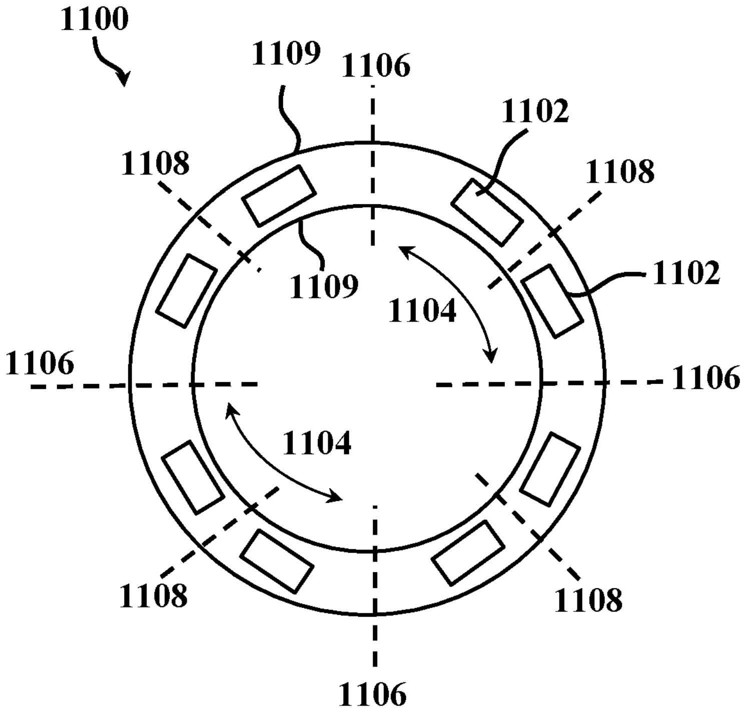
FIGS. 2A-2C are schematic representations (top views) of planar annular base units according to some embodiments of this disclosure.
Figure 2B:
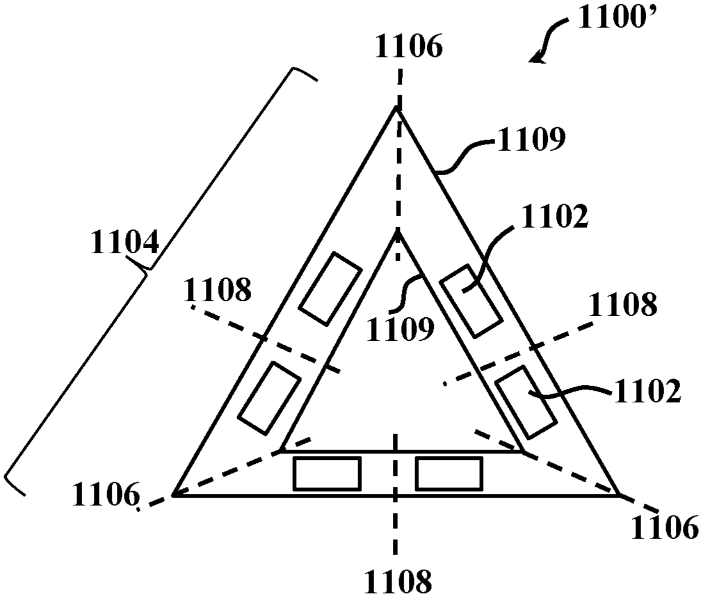
Figure 2C:
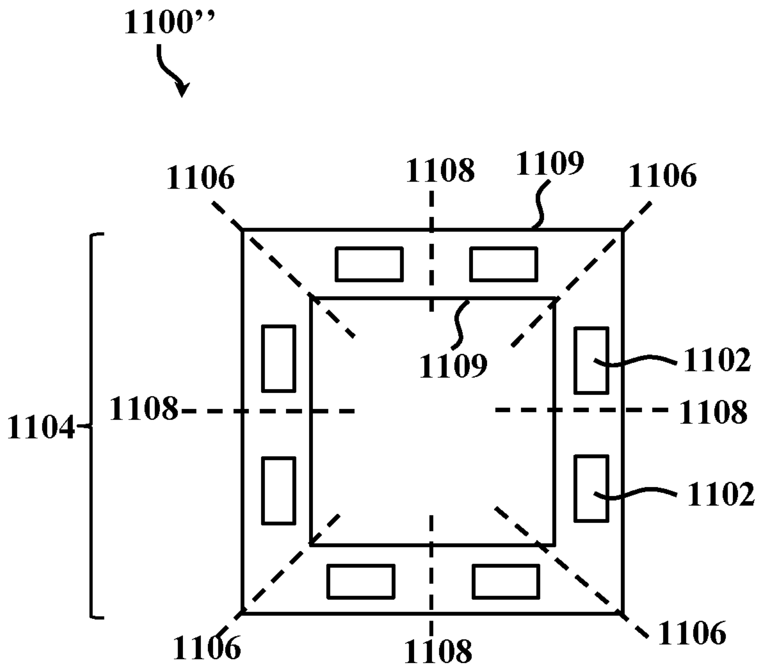

By another embodiment, the annular base unit can have a planar configuration, i.e. formed as a substantially 2D thin annular-shaped object, having a width bounded by two concentric boundaries, as shown in FIGS. 2A-2C. Planar annular base units 1100, 1100' and 1100" (FIGS. 2A, 2B and 2C, respectively), are each constructed as planar annular-shaped objects, with the zones 1102, segments 1104, first fold axes 1106 and second fold axes 1108 arranged along the circumference of the annular base units. The annular base unit is typically made of two or more layers of liquid permeable material, attached, seamed or welded to one another at edges 1109. Detailed description of the folding manner of these planar base units will be detailed below.

Figure 3A:
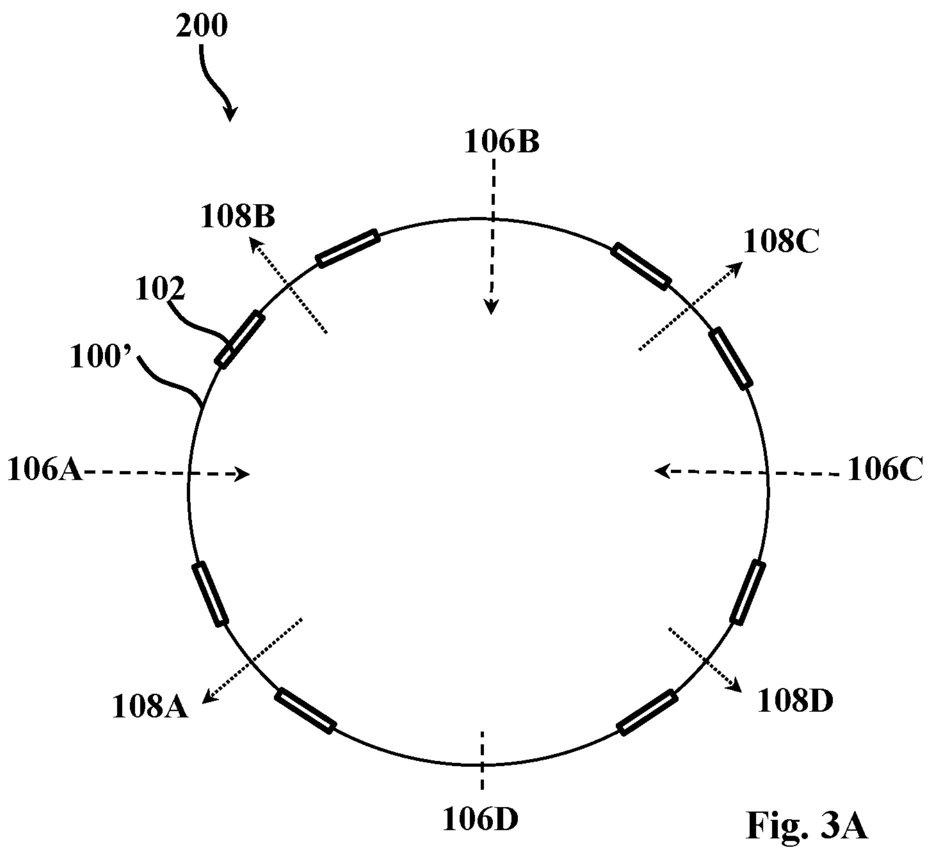
FIGS. 3A-3B is schematic representations of annular basic units, before folding into the primary folded state according to an embodiment of this disclosure.
Figure 3B:
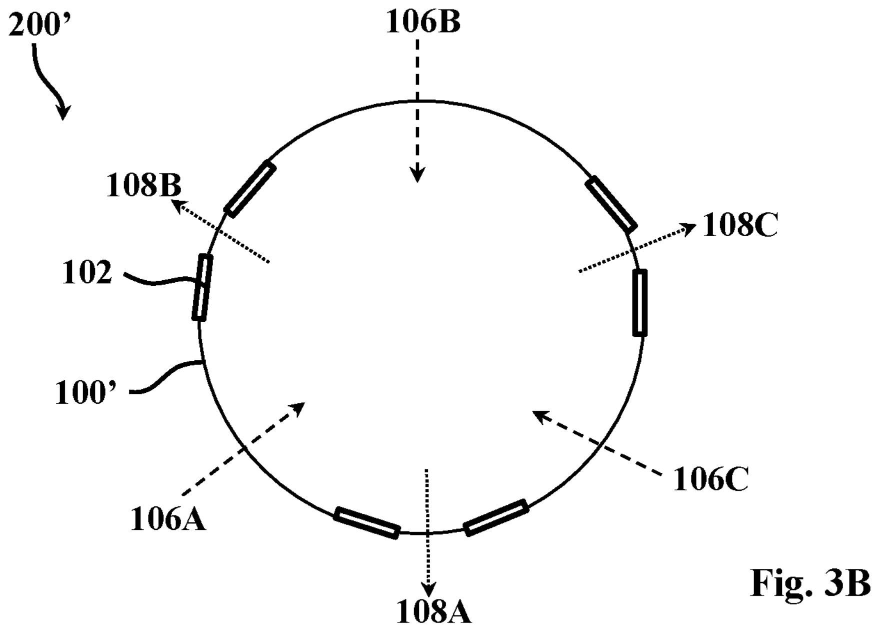

FIG. 3A shows a side view of an annular base unit 200 according to an embodiment of this disclosure, made of strip 100', also showing the first and second fold axes 106A-106C and 108A-108D, respectively. The attachment region of the end portions 112 of the strip constitutes first fold axes 106D. The plurality of zones 102 are distributed along the length of the strip 100'. It is to be understood that each of the zones is constructed as described herein, i.e. comprising a gel-forming material encapsulated between at least two layers of liquid-permeable material. The layers not shown in this figure, and all subsequent figures, for ease of viewing. It is to be understood that while in this specific example eight zones, four first fold axes and four second fold axes are shown, the devices of this disclosure may contain other arrangements (i.e. containing a different number of zones and axes), as long as the alternating arrangement of the first and second axes and the folding principles descried herein are maintained. For example, FIG. 3B depicts an annular base unit comprising of six zones, three first fold axes and three second fold axes.

Figure 4A:
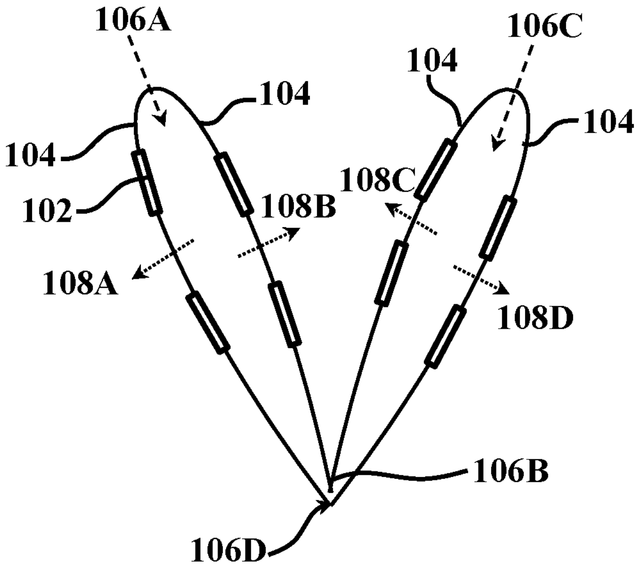
FIGS. 4A-4B show schematic representations of exemplary consecutive stages of folding of the annular basic unit of FIG. 3A into the primary folded state.
Figure 4B:
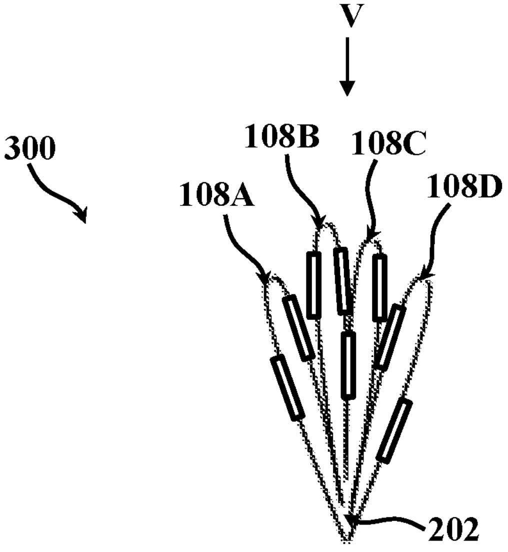
Figure 4C:
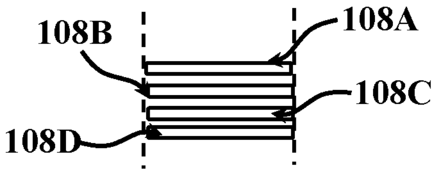
FIG. 4C shows a schematic representation of the primary folded state of FIG. 4B, viewed from the direction marked as "V", showing the stacking of the loops.

FIGS. 4A and 4B are exemplary stages in the folding sequence of annular base unit 200 in order to obtain the device's first folded state. For example, as seen in FIG. 4A, the annular base unit can first be folded along first fold axis 106B, and then along first fold axes 106A and 106C (FIG. 4B). Once thus folded, the first fold axes 106A-106D are adjacent one another and are substantially coaxial along a common axis 202. Such folding results in each segment 104, defined between two consecutive first folding axes 106, assuming a loop-like conformation, with its respective second fold axis 108 defining an apex of the loop. By such folding, the loops are adjacent one another, such that the first fold axes 106 are adjacent (at times co-axial) to one another to form the common axis 202 and the second folding axes 108 extend in an opposite direction to the common axis, such that the loops are stacked one over the other. This configuration constitutes the primary folded state 300 of the device. FIG. 4C provides a view from the direction of arrow V in FIG. 4B. In this view it can be seen that loops, and thus the folded segments, are stacked one over the other, along the thickness direction/dimension of the strip.

As can be seen, due to the folding, zones 102 are distributed along the loop-like folded segments, and positioned in between adjacent loops.

Figure 5A:
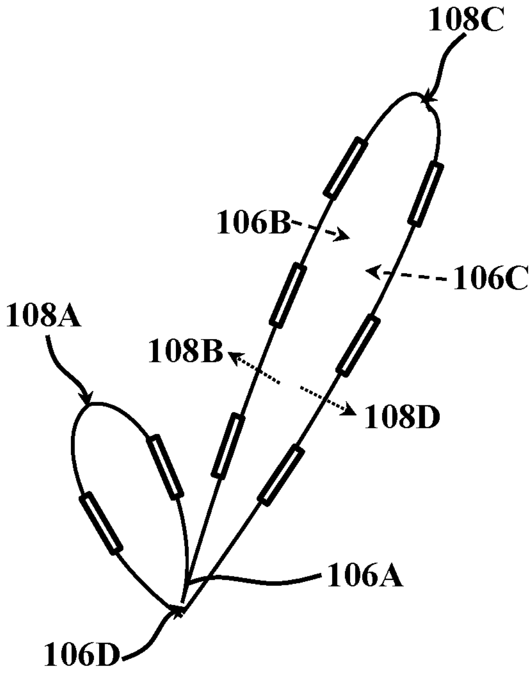
FIGS. 5A-5C show schematic representations of an alternative exemplary consecutive stages of folding of the annular basic unit of FIG. 3 into the primary folded state.
Figure 5B:
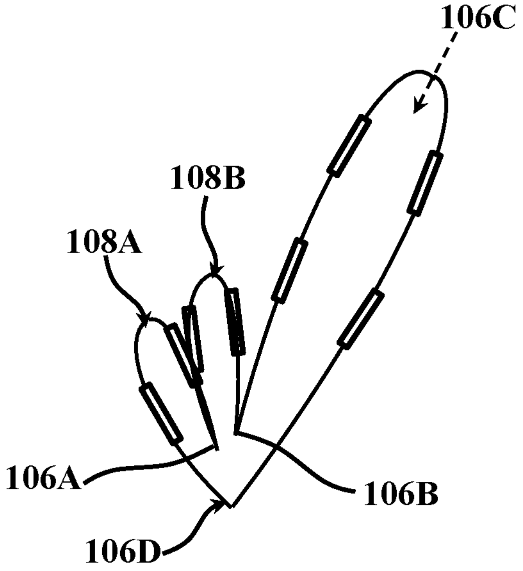
Figure 5C:
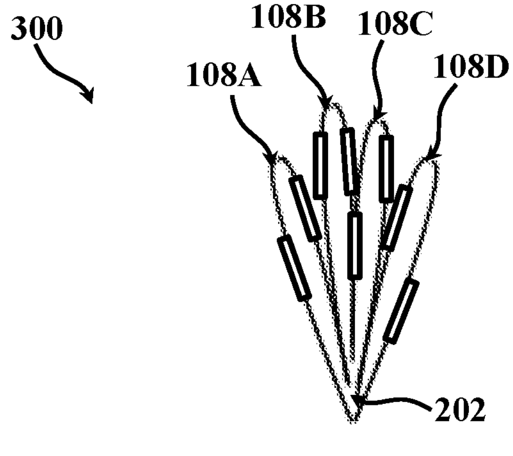

An alternative folding sequence is seen in FIGS. 5A-5C, and follows similar principles of folding shown in FIGS. 4A-4B.

Figure 6A:
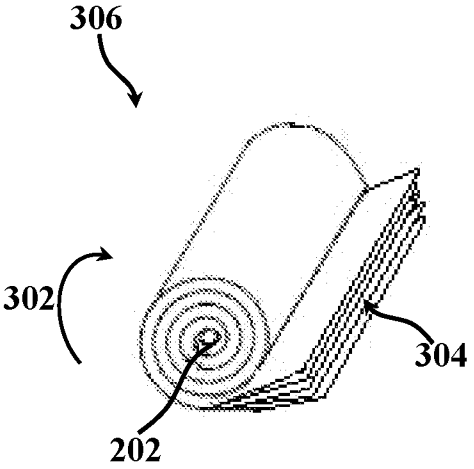
FIGS. 6A-6B show schematic representations of exemplary folding of the device of FIG. 4B (or FIG. 5C) into the secondary folded state (FIG. 6A) and in an encapsulated form (FIG. 6B).
Figure 6B:
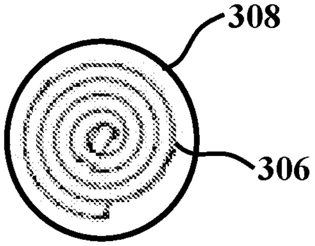

The primary folded device 300 can be further folded, e.g. as shown in FIG. 6A, into a secondary folded state. As shown in FIG. 6A, in the secondary folded state, the device is rolled in the direction of arrow 302 from the common axis 202 towards the apexes 304, thus transforming the device into a rolled-cylindrical configuration. It should be noted that the rolling direction can also be from apexes 304 towards the common axis 202.

As shown in FIG. 6A, once obtaining the secondary folded state, the secondary folded device 306 can be encapsulated in a digestible encapsulation shell, e.g. capsule 308, that can be administered for ingestion by the patient.

After administration, the capsule is ingested and degrades in the stomach to expose the device in its second folded state. Once exposed to liquid in the stomach, the gel-forming material within the zones (that are exposed to the liquid) begins to absorb the liquid and swell. Such swelling starts unrolling the secondary folded device, and concomitantly therewith to push the loop-like folded segments apart one from the other and cause expansion of the device into its expanded state, in which it generally assumes a shape corresponding to its annular basic shape.

In its expanded shape, the swollen zones lead to an increase the volume of the device within the stomach, thereby reducing the volume of the stomach and/or applying pressure onto the walls of the stomach to increase satiation.

A manner of folding a planar annular base unit will now be exemplified. While the specific example in FIGS. 7A-7D are shown with respect to a triangular planar annular base unit, it is understood that the same folding principles can be applied to other planar annular base units, e.g. circular, rectangular, hexagonal, etc.

Figure 7A:
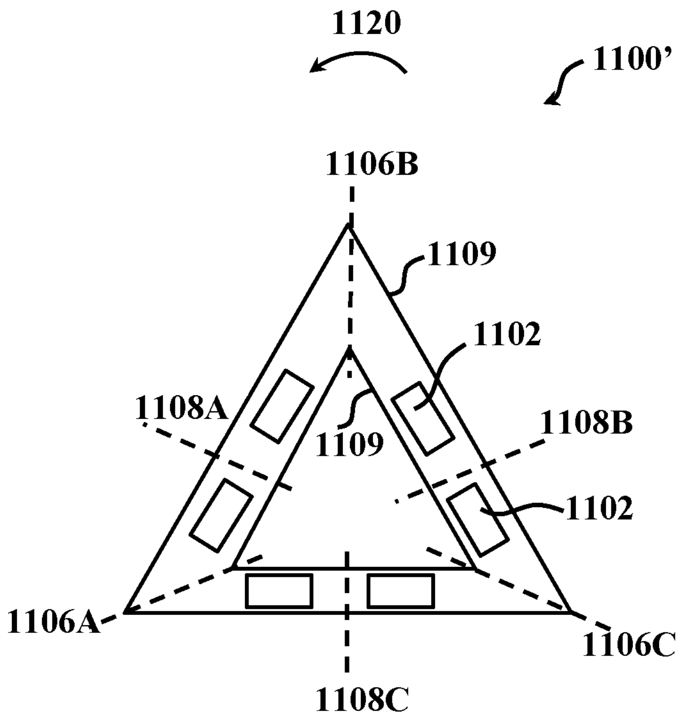
FIGS. 7A-7D show schematic representations of exemplary folding of the device of FIG. 2B into the primary folded state.
Figure 7B:
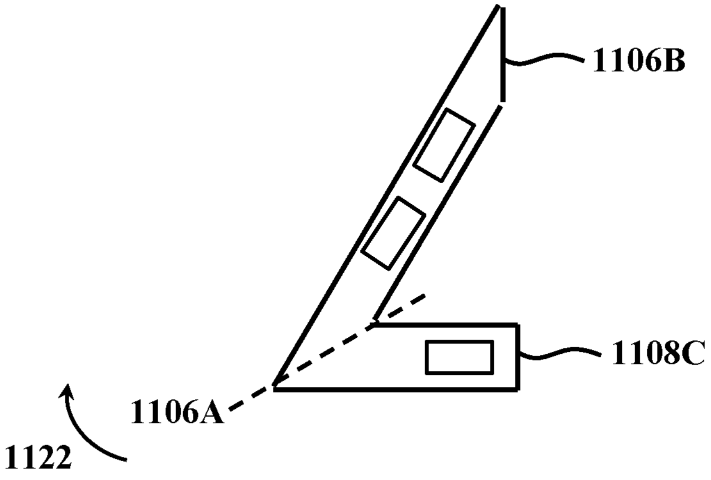
Figure 7C:
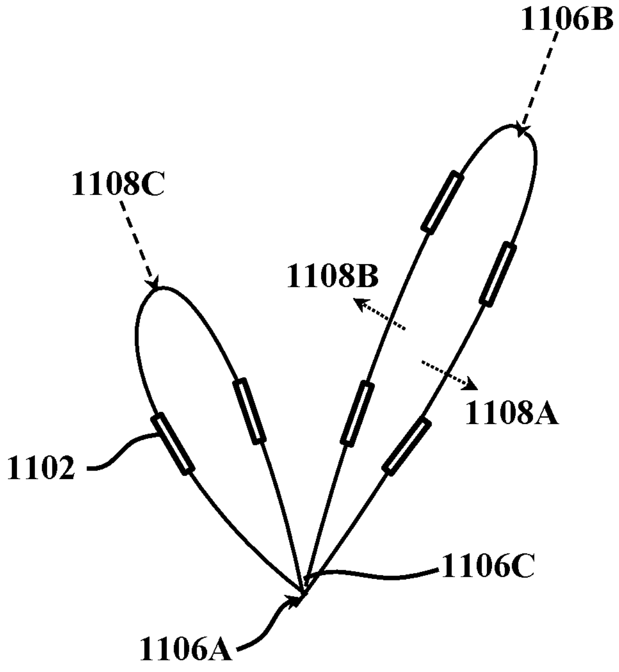
Figure 7D:
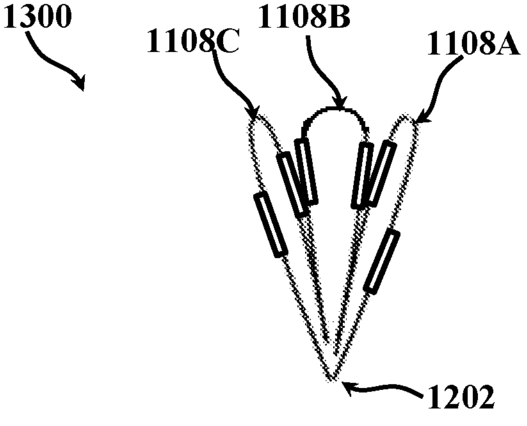

Planar triangular annular base unit 1100' (FIG. 7A) can first be folded along first fold axis 1106C in the direction of arrow 1120, causing axes 1106A and 1106C to overlap one another (FIG. 7B). Then the device is folded about joint axes 1106A,C, in the direction of arrow 1122, to obtain the configuration shown in FIG. 7C. First fold axis 1106B is then folded towards joint axes 1106A,C, thus bringing the first fold axis 1106B to be coaxial along a common axis 1202. Such folding results in each segment defined between two consecutive first folding axes 1106 to assuming a loop-like conformation, with its respective second fold axis 1108 defining an apex of the loop. By such folding, a substantially planar configuration is obtained (FIG. 7D), with the loop-like folded segments being arranged substantially parallel one another along a plane defined between the common axis and the second folding axes. The planar configuration constitutes the primary folded state 1300 of the device.

As can be seen, due to the folding, zones 1102 are distributed along the loop-like folded segments, and positioned in between adjacent loops.

The primary folded device 300 can be further folded into a secondary folded state, by rolling the device from the direction of the common axis 1202 towards the apexes.

The invention claimed is:

1. A biodegradable self-expandable device having a primary folded state and an expanded state, the device comprising:
   - a thin annular base unit, divided into a plurality of consecutive segments along a circumference of the unit,
   - each segment being defined between a pair of successive first fold axes, and each segment comprising one second fold axis, the first and second fold axes being alternatingly arranged along the circumference of the unit, and
   - one or more segments in the plurality of segments include one or more zones that comprise at least one gel-forming material, the gel-forming material in each zone being encapsulated between at least two layers of liquid-permeable material;
   - wherein in the primary folded state of the device, the segments are folded such that the first fold axes extend along a common axis, each folded segment assumes a loop-like conformation with the second fold axis defining an apex of the loop-like conformation, with the folded segments being substantially stacked one over the other,
   - the gel-forming material being configured for swelling upon contact with liquid, to irreversibly switch the device from the primary folded state to the expanded state in which the first fold axes are distanced one from the other, and
   - the annular base unit being formed out of a thin strip having a longitudinal axis, with the first and the second fold axes alternatingly arranged along and perpendicular to the longitudinal axis, the strip extending between matching end portions, the end portions being configured for attachment one to the other to form said annular base unit.

2. The device of claim 1, having a secondary folded state, in which the primary folded device is further rolled in a direction from the common axis towards the apexes.

3. The device of claim 2, further comprising a gastric degradable shell, encapsulating the device in its secondary folded state.

4. The device of claim 1, wherein the liquid-permeable material and/or the gel-forming material is enterically degradable.

5. The device of claim 1, wherein the gel-forming material is in the form of a gel film or gel particles.

6. The device of claim 5, wherein the gel-forming material is in the form of gel particles, the gel particles being embedded within a matrix, forming a substantially continuous gel film.

7. The device of claim 1, wherein the gel-forming material comprises one or more gel forming compounds.

8. The device of claim 1, wherein each segment comprises one or more zones.

9. The device of claim 1, wherein one or more segments in the plurality of segments comprise a plurality of spaced-apart zones.

10. The device of claim 1, wherein, in the expanded state, the device has a circular shape, a polygonal shape, or an irregular shape.

11. The device of claim 1, wherein the matching end portions are configured to form an attachment region, when attached one to the other, the attachment region having a thickness substantially the same as the thickness of the strip.

12. The device of claim 1, wherein the matching end portions are connected one to the other by overlapping the matching end portions one over the other or side-by-side.

13. The device of claim 1, wherein each of the matching end portions comprises at least two layers of liquid-permeable material layers, one of which extending shorter than the other along the end portion, such that the longer layer forms a single-layer terminal section of the end portion.

14. The device of claim 13, wherein the matching end portions are connected one to the other by overlapping the terminal sections side-by-side or one on top of the other.

15. The device of claim 1, wherein the annular base unit is planar.

16. An encapsulated biodegradable self-expandable device, comprising:

an ingestible expandable device according to claim 1, having said primary folded state, a secondary folded state and said expanded state, and a gastric degradable shell encapsulating the device in its secondary folded state, wherein in the primary folded state of the ingestible expandable device, the segments are folded such that the first fold axes extend along a common axis, and each folded segment assumes a loop-like conformation with the second fold axis defining an apex of the loop-like conformation, with the folded segments being substantially stacked one over the other, wherein in the secondary folded state of the ingestible expandable device, the device is further rolled in a direction from the common axis towards the apexes, and wherein in the expanded state, the first fold axes are distanced one from the other, the gel-forming material being configured for swelling upon contact with liquid, to irreversibly switch the ingestible expandable device from the secondary folded state to the expanded state.

17. A preliminary unit being configured for forming an annular base unit that is foldable into a biodegradable self-expandable device of claim 1, the preliminary unit being in the form of a thin strip having a longitudinal axis, the preliminary unit being constructed of porous material that encapsulates regions of at least one gel-forming material, the regions being spaced-apart along the longitudinal axis, each region defining a zone, the gel-forming material in each zone being between at least two layers of liquid-permeable material, the gel-forming material being configured for swelling upon contact with liquid, the strip extending between matching end portions, and the end portions being configured for attachment one to the other to form said annular base unit.

18. The preliminary unit of claim 17, wherein the matching end portions are configured to form an attachment region, when attached one to the other, the attachment region having a thickness substantially the same as the thickness of the strip.

19. The preliminary unit of claim 17, wherein the strip is divided into a plurality of consecutive segments along the longitudinal axis, with alternating first and second fold axes, each of the first fold axes defined between adjacent segments and each segment comprises one second fold axis, and one or more segments in the plurality of segments comprise one or more zones.

* * * * *